United States Patent
Jameel et al.

[11] Patent Number: 5,713,908
[45] Date of Patent: Feb. 3, 1998

[54] LAPARASCOPIC SUTURING INSTRUMENT

[76] Inventors: Irfan Mufty Jameel, 1895 Old Clinton Rd., Apt. A-4, Macon, Ga. 31211; Joe Sam Robinson, Jr., 562 College St., Macon, Ga. 31201

[21] Appl. No.: 805,900

[22] Filed: Feb. 24, 1997

Related U.S. Application Data

[63] Continuation of Ser. No. 374,064, Jan. 9, 1995, abandoned.

[51] Int. Cl.⁶ .................................................. A61B 17/00
[52] U.S. Cl. .......................... 606/148; 606/147; 606/207
[58] Field of Search .................................. 606/147, 148, 606/149, 144, 145, 139, 223; 112/169, 80.03

[56] References Cited

U.S. PATENT DOCUMENTS

| | | |
|---|---|---|
| 253,209 | 2/1882 | Jones . |
| 1,678,361 | 7/1928 | Shearon . |
| 1,822,330 | 9/1931 | Ainslie . |
| 2,213,830 | 9/1940 | Anastasi . |
| 2,738,789 | 3/1956 | Foxworthy . |
| 2,738,790 | 3/1956 | Todt, Sr. et al. . |
| 3,139,089 | 6/1964 | Schwerin . |
| 4,957,498 | 9/1990 | Caspari et al. . |
| 5,015,250 | 5/1991 | Foster . |
| 5,222,962 | 6/1993 | Burkhart . |
| 5,222,977 | 6/1993 | Esser . |
| 5,224,948 | 7/1993 | Abe et al. . |
| 5,234,443 | 8/1993 | Phan et al. . |
| 5,254,126 | 10/1993 | Filipi et al. . |
| 5,281,237 | 1/1994 | Gimpelson . |
| 5,312,422 | 5/1994 | Trott . |
| 5,374,275 | 12/1994 | Bradley et al. . |
| 5,417,701 | 5/1995 | Holmes . |

*Primary Examiner*—Michael Buiz
*Assistant Examiner*—Patrick W. Rasche
*Attorney, Agent, or Firm*—Kennedy, Davis & Kennedy

[57] ABSTRACT

A suturing instrument (10) is disclosed having a handle (11) with finger rings (16, 17), a surgical needle (14) pivotably mounted to the handle, and grasping jaws (12, 13) for securing the pivotal position of the needle. The needle has a suture receiving recess (26) and a latch (27) pivotable between a closed position overlying the recess and an open positioning unobstructing the recess.

16 Claims, 3 Drawing Sheets

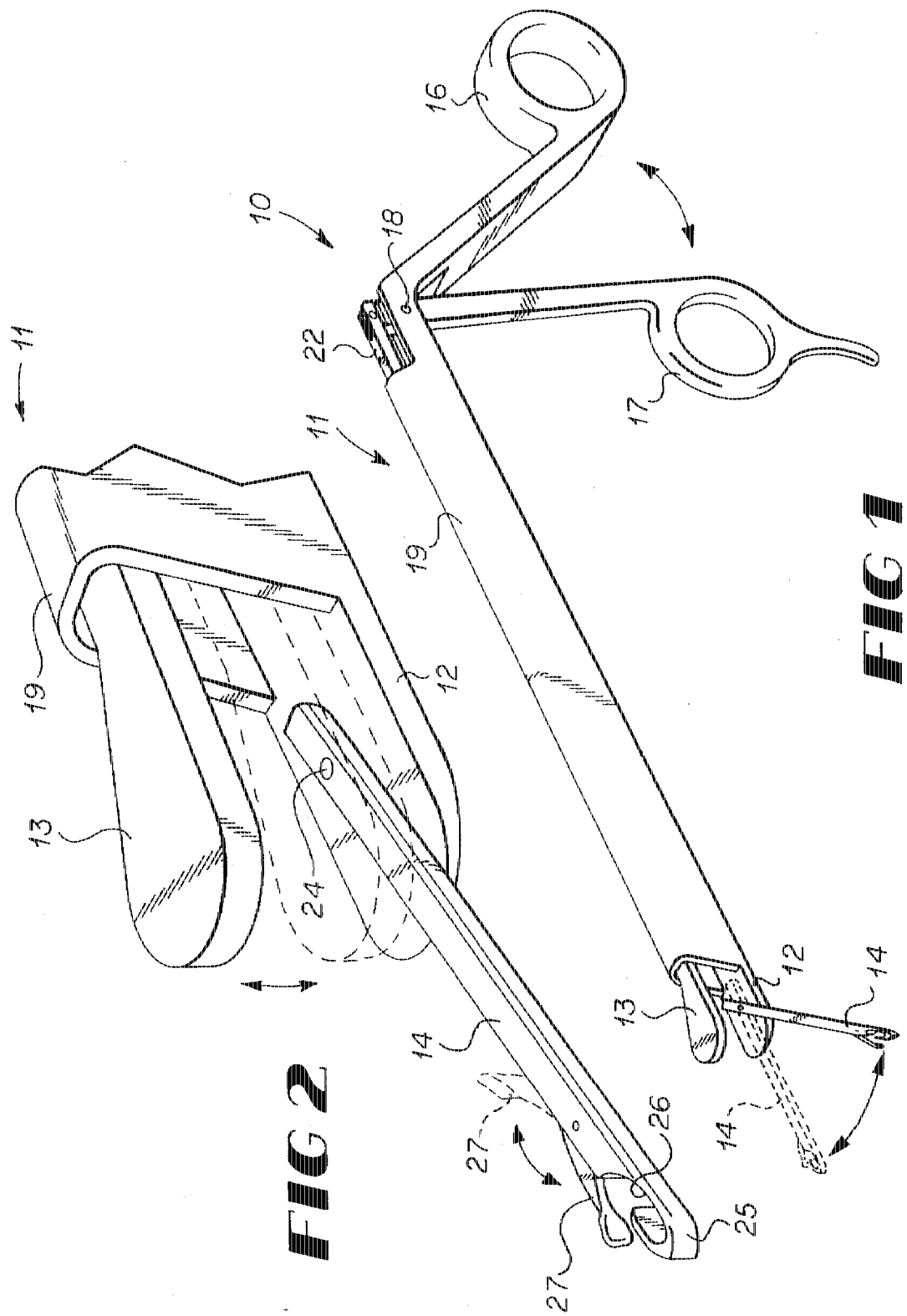

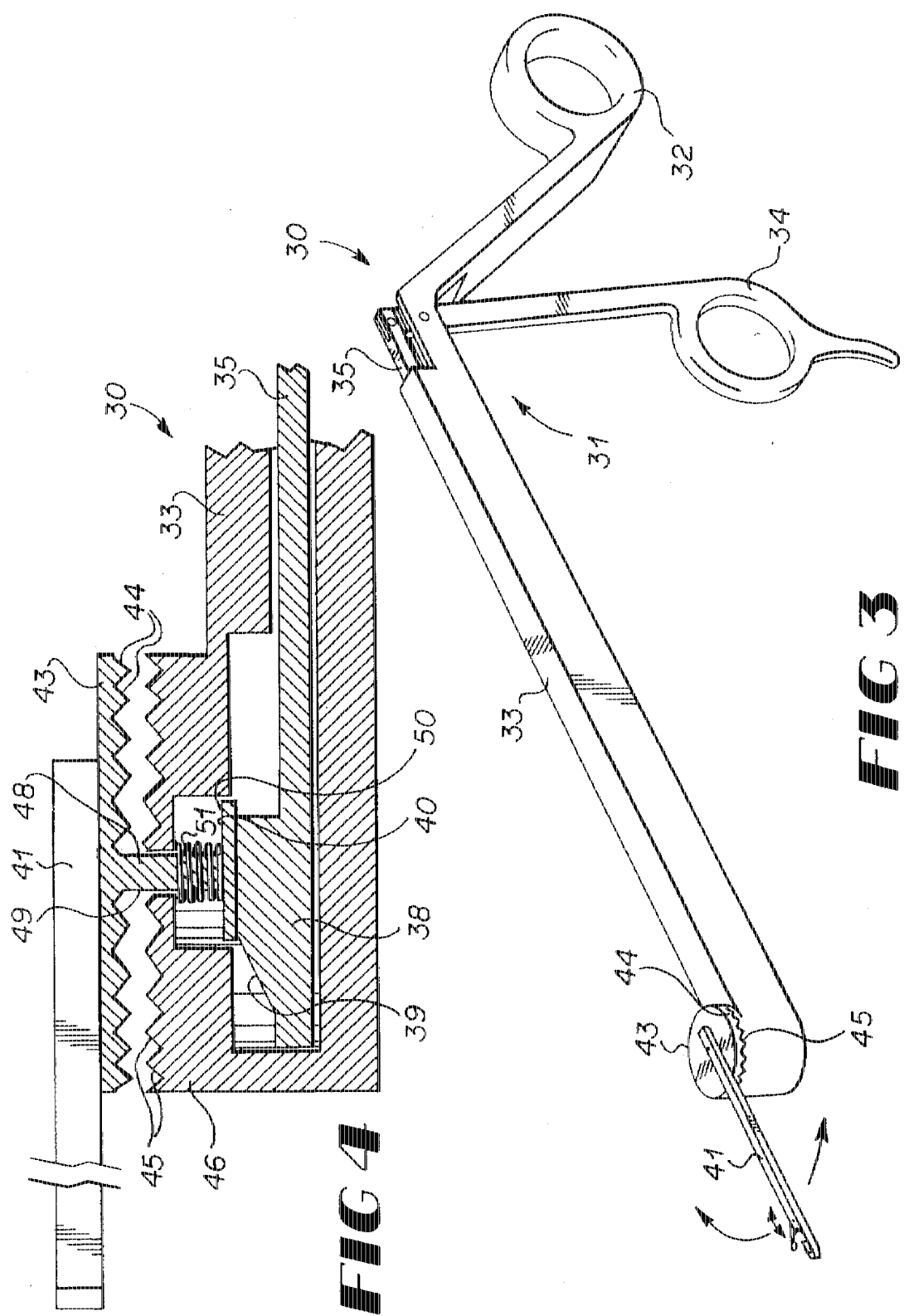

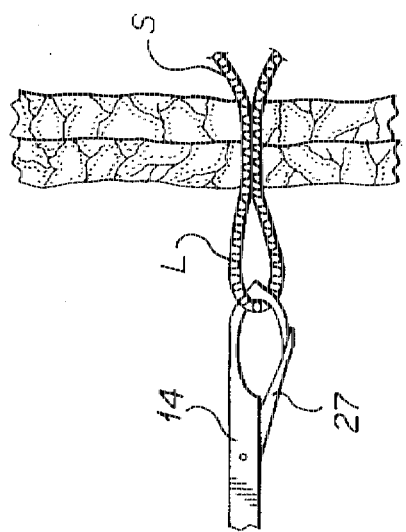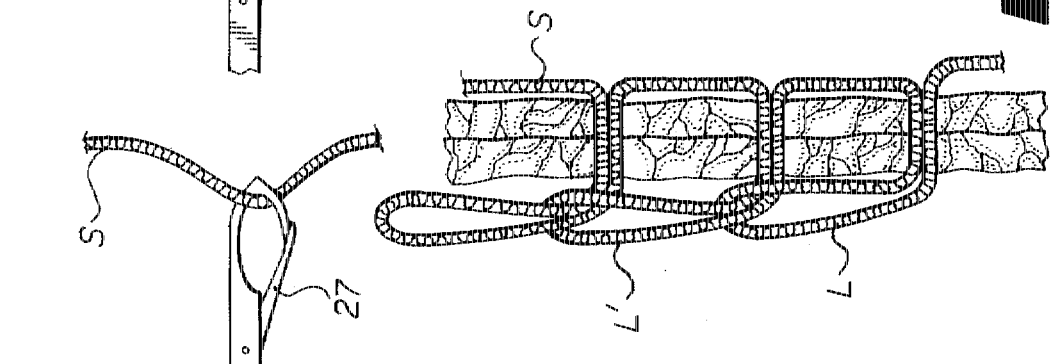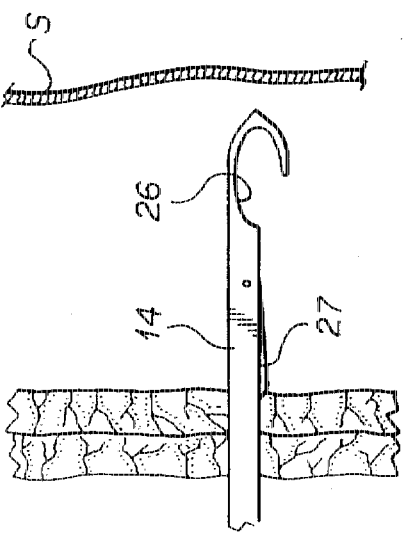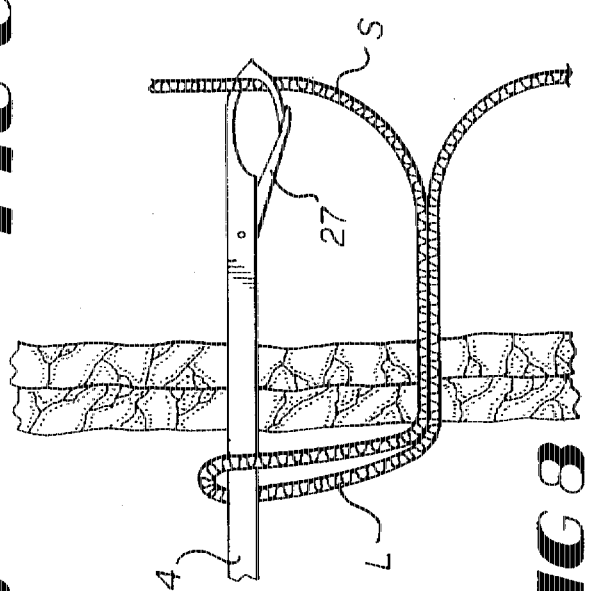

LAPARASCOPIC SUTURING INSTRUMENT

This is a continuation of application Ser. No. 08/374,064, filed Jan. 19, 1995 now abandoned.

TECHNICAL FIELD

This invention relates to instruments used to suture in vivo tissue, and especially to laparoscopic/thoracoscopic instruments used to suture in vivo tissue.

BACKGROUND OF THE INVENTION

Minimal access surgery, such as laparoscopic, arthroscopic, and thoracoscopic surgery and similar minimally invasive surgical techniques, oftentimes requires a physician to suture tissue deep within the body of a patient. Typically, this is done by inserting a trocar into the body, grasping a surgical needle with a suture coupled thereto with a laparoscopic needle holder and passing the laparoscopic needle holder and needle through the trocar to the location of the tissue to be treated. For the needle to pass through the trocar it must be linearly aligned with the needle holder. This method of suturing and the instruments used to do so are described in detail in *Minimally Invasive Surgery* by John G. Hunter and Jonathan M. Sackier, chapters 14 and 15.

During such procedures the needle is typically repositioned intracorporeally relative to the needle holder to suture tissue to the side of the needle holder. Such intracorporeal repositioning of the needle requires the needle to be released from the needle holder, repositioned and regrasped. Similarly, during the suturing procedure itself the needle is pushed through one side of the tissue and regrasped on the opposite side of the tissue. Oftentimes, the needle must be released and regrasped in order to properly position it so that it may once again be pushed through the tissue. Oftentimes however the body does not provide a large enough cavity to accomplish this maneuvering of the needle holder. Also, the releasing of the needle during its initial positioning or its repositioning during the suturing procedure creates the potential hazard of dropping it within the body. Should a needle be dropped it may be difficult to locate or grasp and it may cause damage to the surrounding tissue. Notwithstanding the hazard to the tissue itself this method of repositioning the needle is also very time consuming.

Instruments have also been designed which have a curved needle and a mechanism used to move the curved needle in an arcuate path so as to pierce the tissue and return to the surface, as shown in U.S. Pat. Nos. 1,822,330, 3,139,089 and 5,224,948. However, where a suture must be made to the side of the instrument the entire instrument must be forcibly moved within the body to a position where this may be accomplished. This realigning of the instrument is limited by tissue elasticity and the positioning of the trocar. A repositioning of the instrument beyond these limits may cause damage to the tissue surrounding the instrument or the tissue about the trocar. Thus, to gain access to the tissue it may be necessary to make another incision through which the trocar may be reinserted. This obviously creates additional damage to the tissue and an increase in surgical time.

Accordingly, it is seen that a need remains for an instrument for suturing in vivo tissue in a less intrusive and efficient manner. It is to the provision of such therefore that the present invention is primarily directed.

SUMMARY OF THE INVENTION

In a preferred form of the invention a suturing instrument comprises an elongated handle having a grip end and a support end and a surgical needle. The suturing instrument also has pivotal means for pivotably mounting the surgical needle to the handle support end, holding means for releasably holding the needle in selected pivotal positions with respect to the handle, and locking means for locking and releasing the releasably holding means.

BRIEF DESCRIPTION OF THE DRAWING

FIG. 1 is a perspective view of a suturing instrument embodying principles of the invention is a preferred form.

FIG. 2 is a enlargement of a portion of the suturing instrument of FIG. 1.

FIG. 3 is a perspective view of a suturing instrument embodying principles of the invention in another preferred form.

FIG. 4 is a cross-sectional view of a portion of the suturing instrument of FIG. 3.

FIGS. 5–9 are a sequence of views of a portion of tissue which show, in sequence, tissue being sutured with the needle position of the suturing instrument of FIG. 1 or FIG. 3.

DETAILED DESCRIPTION

With reference to FIGS. 1 and 2 of the drawings, there is shown a suturing instrument 10 having an elongated handle 11, a lower grasping jaw 12, a pivotable, upper grasping jaw 13 and a surgical needle 14 pivotably mounted to lower grasping jaw 12. The elongated handle 11 has fixed finger ring 16 and a movable finger ring 17 pivotably mounted to fixed finger ring 16 by a pivot pin 18. Fixed finger ring 16 integrally extends to an elongated sheath 19 having an integral lower grasping jaw 12. Movable finger ring 17 is pivotally coupled to a push rod 22 which in turn is coupled to upper, grasping jaw 13 so that movement of finger rings 16 and 17 toward each other causes the grasping jaws 12 and 13 to move toward each other. The combination of the handle 11 and grasping jaws 12 and 13 is similar in construction to conventional needle holders shown in *Minimally Invasive Surgery* by John G. Hunter and Jonathan M. Sackier, Chapter 15, FIG. 15–3.

The surgical needle 14 has an elongated shaft 23, a pivot pin 24 extending from the elongated shaft 23 to the lower, grasping jaw 12, a tissue penetrating tip 25, a suture recess 26 and a latch 27 pivotably mounted to shaft 23. The latch 27 is movable between a closed position overlying the recess 26 and an open positioning unobstructing and distal the recess 26 as shown in phantom lines in FIG. 2. The upper and lower grasping jaws cooperate to releasably hold the surgical needle 14 in selected pivotal positions with respect to the handle. The finger rings 16 and 17 in combination with push rod 22 lock and release the upper and lower grasping jaws.

In use, the needle 14 is positioned in linear alignment with handle sheath 19 and the movable finger ring 17 is moved to a position adjacent the fixed finger ring 16. The movement of finger ring 17 moves push rod 22 which in turn pivots the upper grasping jaw 13 into grasping contact with needle 14, i.e. the upper grasping jaw is moved from an ungrasping position to a needle grasping position shown in phantom lines in FIG. 2. The end of the suturing instrument supporting the needle is then passed through a trocar positioned within the body of the patient adjacent the tissue to be treated. A determination of the position of the suturing instrument and a viewing of it throughout the suturing procedure of the tissue is done so in conventional fashion, for example through the use of a endoscope.

Once the suturing instrument 10 is properly positioned within the body the movable finger ring 17 is moved away from the fixed finger ring 16 thereby pivoting the upper grasping jaw 13 to its needle ungrasping position. The needle 14 may now be pivoted to either side, as shown in FIG. 1, so that it may suture adjacent tissue located to the side of the instrument. The movement of the needle 14 may be accomplished in a variety of manners such as with another instrument within the body. The movable finger ring 17 is then moved toward fixed finger ring 16 to once again bring the upper grasping jaw 13 to its needle grasping position thereby securing the needle in its selected pivotal position.

With reference next to FIGS. 5-9, the tissue T is sewn or sutured by positioning the suture S on one side of the tissue T and piercing the opposite side of the tissue with the needle 14, as shown in FIG. 5. As the needle pierces the tissue the latch 27 lies against the needle shaft 23 in its open position to minimize tissue damage. The needle 14 is then maneuvered to grasp the suture S within needle recess 26 and the latch 27 is pivoted to its closed position, as shown in FIG. 6. The latch 27 may be manually pivoted with another instrument or automatically pivoted as it abuts the tissue the needle as it is drawn back through the tissue. As shown in FIG. 7, once the needle is completely drawn back through the tissue the suture S forms a loop L. The suture is then released from the needle by forcing it through the opening of the recess 26 past latch 27. As shown in FIG. 8, the needle 14 is next passed through the suture loop L, piercing the tissue and once again grasping the suture S as previously described. The grasped suture S is brought through the tissue to form another loop L' passing through the previously formed loop L. As shown in FIG. 9, this process is repeated along the entire length of the tissue to be treated. It should be understood that the ends of the suture are tied off in conventional fashion.

With reference next to FIGS. 3 and 4, a suturing instrument 30 in another preferred form is shown. Here, the suturing instrument 30 has an elongated handle 31 with a fixed finger ring 32 integrally extending to a sheath 33, and a movable finger ring 34 pivotable mounted to fixed finger ring 32 which in turn is coupled to a push rod 35. Push rod 35 a camming end 38 having has an inclined camming surface 39 merging with a substantially flat, upper camming surface 40. A surgical needle 41 is pivotably mounted to handle 31 by a disk-shaped upper securing jaw 43 having an annular array of teeth 44 sized and shaped to mate with an annular array of teeth 45 forming a lower securing jaw 46. Hence, the upper and lower securing jaws cooperate to form a detent. The upper securing jaw 43 has a central pivot pin 48 extending through a central opening 49 in the lower securing jaw. Pivot pin 48 has a head 50 and a spring 51 positioned about pivot pin 48 between the lower securing jaw 46 and pivot pin head 50 so as to bias the upper securing jaw toward the lower securing jaw. The upper securing jaw 43 is movable between a disengaged position shown in FIG. 4 and an engaged position shown in FIG. 3 and shown in phantom lines in FIG. 2.

The surgical needle 41 may be pivoted to a desired angle with respect to handle 31 by moving the upper securing jaw to its disengaged position. This is accomplished by moving the movable finger ring 34 towards the fixed finger ring 32 and thus moving camming end 38 of the push rod so as to force the pivot pin head 50 to ride up the inclined camming surface 39 and come to rest upon the upper camming surface 40. The needle may then be pivoted in either direction with the pivot pin head 50 bearing upon the upper camming surface 40. The needle is physically moved as described in reference to the previous embodiment. Once the needle is pivoted to the desired angle it is locked or maintained in this position by moving the upper securing jaw 43 to its engaged position. This is done by moving the movable finger ring 34 away from the fixed finger ring 32 to cause pivot pin 48 to ride off the upper camming surface 40 and back down the inclined camming surface 39 to bring the upper securing jaw into mating engagement with the lower securing jaw.

Hence, it should be understood that the upper and lower securing jaws cooperate to releasably hold the surgical needle 41 in selected pivotal positions with respect to the handle. Also, the finger rings 32 and 34 in combination with push rod 35, and especially the push rod camming end 38, lock and release the upper and lower securing jaws. The suturing procedure is the same as previously described.

While this invention has been described in detail with particular references to the preferred embodiments thereof, it should be understood that many modifications, additions and deletions, in addition to those expressly recited, may be made thereto without departure from the spirit and scope of the invention as set forth in the following claims.

We claim:

1. A suturing instrument comprising an elongated handle having a grip end and a support end; a surgical needle having a tissue piercing tip and an elongated shaft extending from said piercing tip, a portion of said elongated shaft adjacent said tissue piercing tip being aligned along a longitudinal axis extending through said tissue piercing tip; pivot means including a pivot pin extending from said elongated shaft for pivotably mounting said surgical needle to said handle support end for pivotal movement of said shaft portion and piercing tip generally along a radial array of positions about said pivot means; holding means for releasably holding said needle in selected pivotal positions with respect to said handle; and locking means for locking and releasing said releasably holding means, whereby the surgical needle may be pivoted to different radial positions for tissue piercing movement of the surgical needle.

2. The suturing instrument of claim 1 wherein said surgical needle has a thread receiving recess and a latch pivotal between a closed position overlying said recess and an open position distal said recess.

3. The suturing instrument of claim 1 wherein said locking means comprises spring means for biasing said pivot pin and camming means for forcing said pivot pin in a direction opposite to the biasing force of said spring means.

4. The suturing instrument of claim 3 wherein said holding means comprises a detent.

5. The suturing instrument of claim 4 wherein said detent comprises an annular array of teeth coupled to said needle sized and shaped to mate with another annular array of teeth coupled to said handle support end.

6. The suturing instrument of claim 5 wherein said surgical needle has a thread receiving recess and a latch pivotal between a closed position overlying said recess and an open position distal said recess.

7. The suturing instrument of claim 1 wherein said holding means comprises a pair of grasping jaws movable between a position grasping said needle and a position releasing said needle.

8. The suturing instrument of claim 1 wherein said transverse path of travel is generally normal to said longitudinal axis.

9. A suturing instrument comprising an elongated handle having a grip end and a support end; a surgical needle having a tissue piercing tip and an elongated shaft extending from said piercing tip, at least a portion of said elongated shaft adjacent said tissue piercing tip being aligned along a longitudinal axis extending through said tissue piercing tip, pivot means including a pivot pin extending from said elongated shaft coupling said needle to said support end of said handle for pivotal movement of said needle longitudinal axis to a generally radial array of positions about said pivot means; holding means for releasably holding said needle in selected pivotal positions with respect to said handle; and locking means for locking and releasing said releasably holding means, whereby the surgical needle may be pivoted to different radial positions for tissue piercing movement of the surgical needle to different tissue areas about the suturing instrument.

10. The suturing instrument of claim 9 wherein said surgical needle has a thread receiving recess and a latch pivotal between a closed position overlying said recess and an open position distal said recess.

11. The suturing instrument of claim 9 wherein said locking means comprises spring means for biasing said pivot pin and camming means for forcing said pivot pin in a direction opposite to the biasing force of said spring means.

12. The suturing instrument of claim 11 wherein said locking means comprises a detent.

13. The suturing instrument of claim 12 wherein said detent comprises an annular array of teeth coupled to said needle sized and shaped to mate with another annular array of teeth coupled to said handle support end.

14. The suturing instrument of claim 13 wherein said surgical needle has a thread receiving recess and a latch pivotal between a closed position overlying said recess and an open position distal said recess.

15. The suturing instrument of claim 9 wherein said holding means comprises a pair of grasping jaws movable between a position grasping said needle and a position releasing said needle.

16. The suturing instrument of claim 9 wherein said transverse path of travel is generally normal to said longitudinal axis.

* * * * *